US006465437B1

(12) United States Patent
Rafka et al.

(10) Patent No.: US 6,465,437 B1
(45) Date of Patent: Oct. 15, 2002

(54) DIPHOSPHATE SALT OF A 4"-SUBSTITUTED-9-DEOXO-9A-AZA-9A-HOMOERYTHROMYCIN DERIVATIVE AND ITS PHARMACEUTICAL COMPOSITION

(75) Inventors: Robert J. Rafka, Stonington, CT (US); Colman B. Ragan, Mystic, CT (US); Douglas J. M. Allen, New London, CT (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 09/574,160

(22) Filed: May 18, 2000

Related U.S. Application Data

(60) Provisional application No. 60/141,681, filed on Jun. 30, 1999.

(51) Int. Cl.$^7$ ................................................ A01N 43/04
(52) U.S. Cl. ........................... 514/29; 536/7.2; 536/7.4; 536/124
(58) Field of Search .......................... 536/7.4, 7.2, 124; 514/29

(56) References Cited

FOREIGN PATENT DOCUMENTS

WO        WO 98/56802        * 12/1998

* cited by examiner

*Primary Examiner*—Jezia Riley
(74) *Attorney, Agent, or Firm*—Peter C. Richardson; Gregg C. Benson; Robert T. Barker

(57) ABSTRACT

This invention relates to a novel crystalline diphosphate salt of (2R,3S,4R,5R,8R,10R,11R,12S,13S,14R)-13-[[2,6-dideoxy-3-C-methyl-3-O-methyl-4-C-[(propylamino) methyl]-α-L-ribo-hexopryanosyl]oxy]-2-ethyl-3,4,10-trihydroxy-3,5,8,10,12,14-hexamethyl-11-[[3,4,6-trideoxy-3-(dimethylamino)-β-D-xylo-hexopyranosyl]oxy]-1-oxa-6-azacyclopentadecan-15-one that is useful as an antibacterial and antiprotozoal agent in mammals. This invention also relates to pharmaceutical compositions containing the free base of the diphosphate salt and the methods of treating bacterial and protozoal infections in mammals by administering the free base of the diphosphate to mammals requiring such treatment. The free base of the diphosphate salt of the present invention possesses potent activity against various bacterial and protozoal infections when given by parenteral application to mammals.

15 Claims, No Drawings

DIPHOSPHATE SALT OF A 4"-SUBSTITUTED-9-DEOXO-9A-AZA-9A-HOMOERYTHROMYCIN DERIVATIVE AND ITS PHARMACEUTICAL COMPOSITION

This application claims the benefit of U.S. Provisional Patent Application No. 60/141,681 filed Jun. 30, 1999.

This invention relates to a novel crystalline diphosphate salt of (2R,3S,4R,5R,8R,10R,11R,12S,13S,14R)-13-[[2,6-dideoxy-3-C-methyl-3-0-methyl-4-C-[(propylamino) methyl]-α-L-ribo-hexopryanosyl]oxy]-2-ethyl-3,4,10-trihydroxy-3,5,8,10,12,14-hexamethyl-11-[[3,4,6-trideoxy-3-(dimethylamino)-β-D-xylo-hexopyranosyl]oxy]-1-oxa-6-azacyclopentadecan-15-one (hereinafter the diphosphate salt) that is useful as an antibacterial and antiprotozoal agent in mammals. This invention also relates to pharmaceutical compositions containing the free base of the diphosphate salt and the methods of treating bacterial and protozoal infections in mammals by administering the free base of the diphosphate salt to mammals requiring such treatment. The free base of the diphosphate salt of the present invention possesses potent activity against various bacterial and protozoal infections when given by parenteral application to mammals.

Macrolide antibiotics are known to be useful in the treatment of a broad spectrum of bacterial and protozoal infections in mammals, fish and birds. Such antibiotics include various derivatives of erythromycin A such as azithromycin which is commercially available and is referred to in U.S. Pat. Nos. 4,474,768 and 4,517,359 both of which are incorporated herein by reference in their entirety.

SUMMARY OF THE INVENTION

The present invention relates to two polymorphs of (2R,3S,4R,5R,8R,10R,11R,12S,13S,14R)-13-[[2,6-dideoxy-3-C-methyl-3-0-methyl-4-C[(propylamino)methyl]-α-L-ribo-hexopryanosyl]oxy]-2-ethyl-3,4,10-trihydroxy-3,5,8,10,12,14-hexamethyl-11-[[3,4,6-trideoxy-3-(dimethylamino)-β-D-xylo-hexopyranosyl]oxy]-1-oxa-6-azacyclopentadecan-15-one diphosphate (hereinafter the diphosphate salt) shown below:

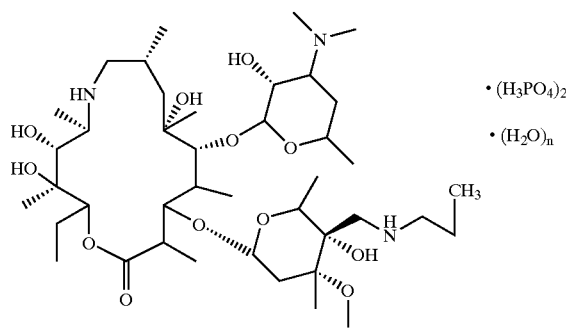

Wherein n is 0 to 8.

In one embodiment of the invention, the diphosphate salt is a liquid crystal that has a lath-like habit and exhibits longitudinal cleavage but no lateral cleavage. X-ray diffraction shows little or no order.

In another embodiment, the disphosphate salt is crystalline. Microscopy of the diphosphate salt indicates a plate or prism habit, both of which are highly birefringent. The diphosphate salt is a well-ordered crystal characterized by the X-ray diffraction pattern below:

| Peak No. | 1 | 2 | 3 | 4 | 5 | 6 | 7 | 8 | 9 | 10 |
|---|---|---|---|---|---|---|---|---|---|---|
| d space | 16.2 | 12.4 | 10.8 | 9.0 | 6.9 | 6.5 | 6.2 | 5.4 | 5.1 | 4.9 |

The crystalline diphosphate salt gradually absorbs water to about 13% at 87% relative humidity with a rapid uptake of water to about 48% occurring at about 90% relative humidity. Thermogravametric analysis on the diphosphate salt discloses that three waters are lost by about 75° C., a fourth water is lost by about 120° C., the fifth water is lost by about 170° C., and the final three waters are lost by about 200° C. The maximum number of water molecules necessary for the stabilization of the crystalline lattice appears to be about eight. Drying the diphosphate salt in about 70° C. in air or about 45° C. in a vacuum removed the water leaving a pseudomorph. The crystalline diphosphate salt has an aqueous solubility of about 280mg/mL.

A method of preparing the diphosphate salt comprises dissolving the anhydrous free base with magnetic stirring in absolute ethanol at ambient temperature, adding a solution of phosphoric acid in absolute ethanol over about 2 to 5 minutes to afford a precipitate, then partially dissolving the resulting solid in a small proportion of water. Stirring for several hours at ambient temperature affords a crystal crop that is collected by filtration then rinsed with several small portions of about 10/1 (v/v) ethanol-water. After the diphosphate salt has been synthesized it is reconverted to a pharmaceutically acceptable free base by a method which comprises dissolution in water, addition of methylene chloride, increasing the pH to about 8.5 to 10, collection and concentration of the organic phase, and crystallization of the amorphous free base from a hydrocarbon solvent.

A pharmaceutical composition which has antibacterial and antiprotozoal activity in mammals comprises the free base of the diphosphate salt in an amount effective in the treatment of bacterial and protozoal diseases and a pharmaceutically acceptable carrier. A method of treating bacterial and protozoal infections comprises administering to mammals in need of such treatment an antibacterial amount of the free base of the diphosphate salt. The antibacterial amount of the free base is given by parenteral application to mammals.

DETAILED DESCRIPTION OF THE INVENTION

The present invention relates to two polymorphs of (2R,3S,4R,5R,8R,10R,11R,12S,13S,14R)-13-[[2,6-dideoxy-3-C-methyl-3-0-methyl-4-C-[(propylamino)methyl]-α-L-ribo-hexopryanosyl]oxy]-2-ethyl-3,4,10-trihydroxy-3,5,8,10,12,14-hexamethyl-11-[[3,4,6-trideoxy-3-(dimethylamino)-β-D-xylo-hexopyranosyl]oxy]-1-oxa-6-azacyclopentadecan-15-one diphosphate shown below:

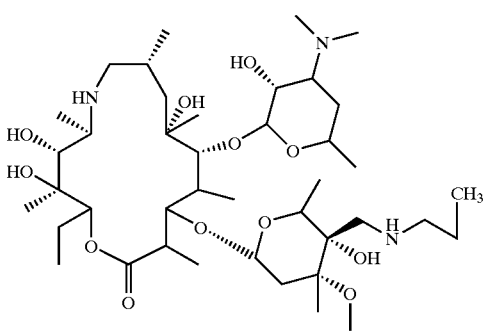

wherein n is 0 to 8.

In one embodiment of the invention, the diphosphate salt is a liquid crystal that has a lath-like habit and exhibits longitudinal cleavage but no lateral cleavage. X-ray diffraction shows little or no order.

In another embodiment, the diphosphate salt is a crystalline hygroscopic salt. Microscopy of the diphosphate salt indicates a plate or prism habit both of which are highly birefringent. The diphosphate salt is a well ordered crystal characterized by the X-ray diffraction pattern below:

| Peak No. | 1 | 2 | 3 | 4 | 5 | 6 | 7 | 8 | 9 | 10 |
|---|---|---|---|---|---|---|---|---|---|---|
| d space | 16.2 | 12.4 | 10.8 | 9.0 | 6.9 | 6.5 | 6.2 | 5.4 | 5.1 | 4.9 |

The invention also relates to processes for preparing the liquid crystal and the crystalline diphosphate salt as well as the pharmaceutical composition of the free base of the diphosphate salt as shown in Scheme 1 below:

Scheme 1

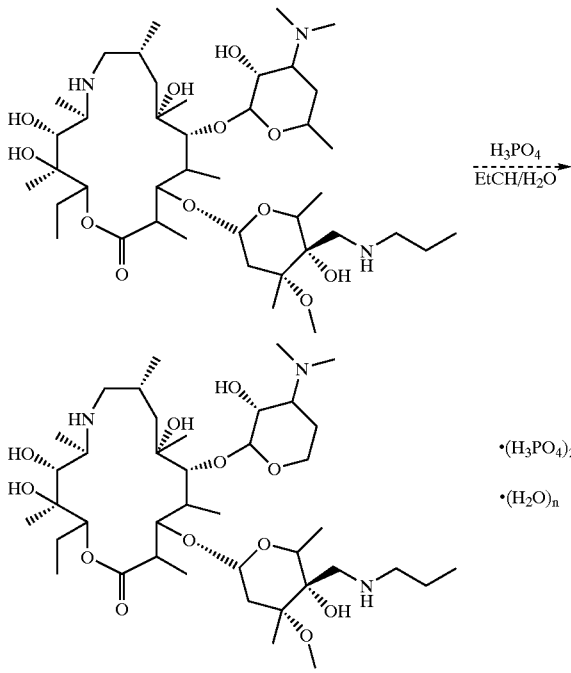

Wherein n is 0–8.

Differential scanning calorimetry of the crystalline diphosphate salt shows a single event at about 119° C. which coincides with water loss as well as the dissolution of the salt in the released water. No crystallization follows the event.

Drying in the VTI at 20–25° C. indicated a weight loss of 10%; the dried salt gradually adsorbed water to 15% at 85% RH (relative humidity), followed by a rapid uptake to 48% at 90% RH. At 90% RH, the compound deliquesced.

The diphosphate salt was also studied by thermogravametic analysis (TGA). On samples rehydrated at 87% RH [13% water by Karl Fisher (KF) titration], four distinct breaks were noted. There were 3 waters lost by about 75° C.; 4 by about 120° C., 5 by about 170° C., and 8 lost by about 200° C. The maximum water molecules necessary for the stabilization of the crystalline lattice appears to be eight. A reduction in the water level of the hydrate caused no change in the X-ray diffraction data indicating the formation of a pseudomorph of the hydrate.

The mobility of the water within the crystalline lattice is directly related to the relative humidity of the environment the diphosphate salt comes in contact with. For example, at about 87% relative humidity, the compound contains about 13% water; at 60% relative humidity the compound contains about 8% water; and at 40% relative humidity the diphosphate salt contains about 5% water (all calculations by KF).

Drying the diphosphate salt at 70° C. in air or at 45° C. under vacuum removed all the water leaving a psuedomorph. Rehydrating the salt at about 87% relative yielded the octahydrate form.

The following examples illustrate the methods and compounds of the present invention. It will be understood that the invention is not limited to the specific examples.

EXAMPLE 1

Liquid Crystals of the Diphosphate Salt (2R,3S,4R,5R,8R,10R,11R,12S,13S,14R)-13-[[2,6-dideoxy-3-C-methyl-3-0-methyl-4-C-[(propylamino)methyl]-α-L-ribohexopryanosyl]oxy]-2-ethyl-3,4,10-trihydroxy-3,5,8,10,12,14-hexamethyl-11-[[3,4,6-trideoxy-3-(dimethylamino)-β-D-xylohexopyranosyl]oxy]-1-oxa-6-azacyclopentadecan-15-one (7.5 g, 97%, 9.0 mmol) was dissolved in absolute ethanol (190 mL) at ambient temperature. A 15 mL portion of a solution of phosphoric acid in absolute ethanol (7.15 g of commercial $H_3PO_4$ diluted to 100 mL, 9.3 mmol, 1.03 eq) was then added. A white precipitate formed immediately. Water (10 mL) was added after stirring the suspension at ambient temperature for 1 hour. The mixture then stirred for 6 days, after which the solids were collected on a Buchner funnel and rinsed twice with small portions of absolute ethanol. The damp filter cake was dried under high vacuum at ambient temperature. The resultant solids exhibited birefringence under cross polarizing light but did not exhibit an X-ray diffraction pattern.

KF analysis on the liquid crystals indicated that they contained 5.5% water. Calculated and actual values for elemental analysis are shown below:

|  | % calculated | % observed |
|---|---|---|
| C | 46.44 | 48.15 |
| H | 8.69 | 9.22 |
| N | 3.96 | 4.11 |
| P | 5.84 | 5.83 |

An HPLC potency assay was also performed. The expected potency of a diphosphate salt containing 5.5% water was 76.4%; the observed value was 76.9%.

Subsequent lots that were air-dried only also exhibited no X-ray pattern. A small portion of the liquid crystals was placed in a test tube and was dissolved (with warming) in 1-propanol (containing a small proportion of water) then left out in a hood to slowly evaporate. Solids from this trial were used as seed crystals in Example 2.

EXAMPLE 2

Crystalline Diphosphate Octahydrate Salt

The free base (10 g, 98.8%, 12.3 mmol) was dissolved, with magnetic stirring, in absolute ethanol (180 mL) at ambient temperature. A solution of phosphoric acid in absolute ethanol [18 mL, 11.2 mmol, 0.9 eq (7.15 g $H_3PO_4$ diluted to 100 mL)] was added over about 3 minutes which caused the formation of a white, sticky precipitate. Water (10 mL) was added and the mixture was stirred at ambient temperature overnight. The crystal crop was collected on a Buchner funnel and the solids rinsed with three small portions of 10/1 (v/v) ethanol-water. The recovered, air-dried solids weighed 2.09 g. X-Ray analysis of the solids indicated the presence of the liquid crystal form. A 500 mg sample of the liquid crystals was dissolved (with warming) in 2 mL of 10:1 (v/v) ethanol-water. The resultant solution was cooled to ambient temperature and seeded with solids from the small-scale trial involving wet 1-propanol. The mixture stirred at ambient temperature overnight. The resultant solids were collected on a Buchner funnel and rinsed with a small proportion of 10:1 (v/v) ethanol-water and air-dried to a weight of 370 mg. X-Ray analysis indicated that the material was now well-ordered and exhibited a well-defined powder pattern as shown below:

| Peak No. | 1 | 2 | 3 | 4 | 5 | 6 | 7 | 8 | 9 | 10 |
|---|---|---|---|---|---|---|---|---|---|---|
| d space | 16.2 | 12.4 | 10.8 | 9.0 | 6.9 | 6.5 | 6.2 | 5.4 | 5.1 | 4.9 |

Both the liquid crystal and the crystalline form of the diphosphate were hygroscopic. When attempts were conducted in hydrophilic solvents, the addition of 4% to 5% (v/v) water to the amorphous slurry caused the compound to crystallize as an octahydate. Crystallization in ethanol/water indicated that a metastable ethanol solvate could form.

EXAMPLE 3

Purified Crystalline Diphosphate Octahydrate

A 1.18 g portion of amorphous diphosphate octahydrate was combined with 18.5 mL of absolute ethanol and 1.05 mL of water. The mixture was heated to reflux for 15 minutes to yield a hazy solution. The heat was removed and the stirred mixture cooled to ambient temperature to promote crystallization. After a 2 hour granulation, the product was cooled, filtered, and air dried under ambient conditions to afford the pure diphosphate octahydrate salt.

EXAMPLE 4

The Free Base of (2R,3S,4R,5R,8R,10R,11R,12S,13S,14R)-13-[[2,6-dideoxy-3-C-methyl-3-0-methyl-4-C-[(Propylamino)methyl]-α-L-ribo-hexopryanosyl]oxy]-2-ethyl-3,4,10-trihydroxy-3,5,8,10,12,14-hexamethyl-11-[[3,4,6-trideoxy-3-(dimethylamino)-(β-D-xylo-hexopyranosyl]oxy]-1-oxa-6-azacyclopentadecan-15-one The diphosphate salt (225 g) was partitioned between water (1200 mL) and methylene chloride (500 mL). The pH of the aqueous phase was raised from 5.9 to 8.6 by addition of solid potassium carbonate. The organic phase was collected, dried over anhydrous sodium sulfate and concentrated to a dry, amorphous foam (170 g).

EXAMPLE 5

The amorphous free base (170 g) was crystallized from heptane (700 mL) to generate clean, crystalline free base (115 g) which was then formulated as a partially aqueous solution for parenteral use in livestock.

The above process and resulting diphosphate salt possess valuable and nonobvious properties. Formation of the diphosphate salt allows a large number of impurities to be purged in the resultant mother liquor. Upon reconversion to the free base, this results in a drug substance that forms very low levels of haze upon formulation in partially aqueous media. This results in a pharmaceutically superior solution for parenteral application.

The active compounds may be administered alone or in combination with pharmaceutically acceptable carriers or diluents by the routes previously indicated, and such administration may be carried out in single or multiple doses. More particularly, the active compounds may be administered in a wide variety of different dosage forms, i.e., they may be combined with various pharmaceutically acceptable inert carriers in the form of tablets, capsules, lozenges, troches, hard candies, powders, sprays, creams, salves, suppositories, jellies, gels, pastes, lotions, ointments, aqueous suspensions, injectable solutions, elixirs, syrups, and the like. Such carriers include solid diluents or fillers, sterile aqueous media and various non-toxic organic solvents, etc. Moreover, oral pharmaceutical compositions can be suitably sweetened and/or flavored. In general, the active compounds are present in such dosage forms at concentration levels ranging from about 5.0% to about 70% by weight.

For parenteral administration, solutions of an active compound in an oil, a partially aqueous vehicle, or an aqueous vehicle may be employed. The oil will be selected from those which are pharmaceutically acceptable; for example sesame or peanut oil may be employed. The non aqueous component of a partially aqueous vehicle will be selected those which are pharmaceutically acceptable; for example, propylene glycol or polyethylene glycol, may be employed. The aqueous solutions should be suitably buffered (preferably pH less than 8) if necessary. The aqueous and partially aqueous solutions are suitable for intravenous injection purposes. The aqueous, partially aqueous, and oily solutions are suitable for intraarticular, intramuscular and subcutaneous injection purposes. The preparation of all these solutions under sterile conditions is readily accomplished by standard pharmaceutical techniques well known to those skilled in the art.

We claim:

1. Two polymorphs of (2R,3S,4R,5R,8R,10R,11R,12S,13S,14R)-13-[[2,6-dideoxy-3-C-methyl-3-O-methyl-4-C-[(propylamino)methyl]-α-L-ribo-hexopryanosyl]oxy]-2-ethyl-3,4,10-trihydroxy-3,5,8,10,12,14-hexamethyl-11-[[3,4,6-trideoxy-3-(dimethylamino)-β-D-xylo-hexopyranosyl]oxy]-1-oxa-6-azacyclopentadecan-15-one diphosphate having the formula

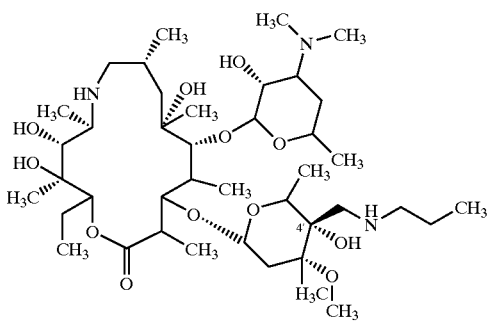

wherein n is 0 to 8 and the polymorphs are selected from the group consisting of:
 a. a smectic crystalline meso phase of a liquid crystal; and
 b. a crystalline diphosphate exhibiting the X-ray powder diffraction pattern

| Peak No. | 1 | 2 | 3 | 4 | 5 | 6 | 7 | 8 | 9 | 10 |
|---|---|---|---|---|---|---|---|---|---|---|
| d space | 16.2 | 12.4 | 10.8 | 9.0 | 6.9 | 6.5 | 6.2 | 5.4 | 5.1 | 4.9 |

2. The diphosphate liquid crystal according to claim 1 having a lath-like habit and exhibiting longitudinal cleavage.

3. The diphosphate liquid crystal according to claim 2 gaining about 15% by weight with a subsequent loss of birefringence at about 87% relative humidity.

4. The diphosphate salt according to claim 2, wherein the liquid crystal has about 5 to 6% water.

5. The diphosphate salt according to claim 1 wherein the salt has about 48% C, about 9% H, about 4% N, about 6% P and about 5.5% $H_2O$.

6. The diphosphate salt polymorph according to claim 1 having a well-ordered crystalline plate or prism habit.

7. The diphosphate salt according to claim 6 wherein the plate or prism habit is highly birefringent.

8. The crystalline diphosphate salt according to claim 1, wherein the compound gradually absorbs water to about 13% at about 87% relative humidity.

9. The diphosphate salt according to claim 8, wherein a rapid uptake of water to about 48% occurs at about 90% relative humidity.

10. The diphosphate salt according to claim 9 wherein the diphosphate salt became deliquescent at about 90% relative humidity.

11. The diphosphate salt according to claim 1 wherein thermogravametric analysis discloses that 3 waters are lost by about 75° C., a fourth water is lost by about 120° C., a fifth water is lost by about 170° C., and the three final waters are lost by about 200° C.

12. The diphosphate salt according to claim 1 wherein the maximum number of water molecules necessary for the stabilization of the crystalline lattice is eight.

13. The diphosphate salt according to claim 1 wherein drying in about 70° C. in air or about 45° C. in a vacuum removed the water leaving a psuedomorph.

14. The diphosphate salt according to claim 1 wherein the aqueous solubility is about 280 mg/mL.

15. A pharmaceutical composition having antibacterial and antiprotozoal activity in mammals comprising the free base of the diphosphate salt according to claim 1 in an amount effective in the treatment of bacterial and protozoal diseases and a pharmaceutically acceptable carrier.

* * * * *